United States Patent
Tison et al.

(10) Patent No.: US 7,482,021 B1
(45) Date of Patent: Jan. 27, 2009

(54) TWO-SIDED WIPE FOR CLEANING AND DRYING A SKIN SURFACE

(76) Inventors: Kelley H. Tison, 103 Melbourne Pl., Athens, GA (US) 30606; James R. Hunt, 1575 Chevon Dr., Dunwoody, GA (US) 30350

( * ) Notice: Subject to any disclaimer, the term of this patent is extended or adjusted under 35 U.S.C. 154(b) by 347 days.

(21) Appl. No.: 11/187,193

(22) Filed: Jul. 22, 2005

Related U.S. Application Data

(63) Continuation of application No. 10/144,002, filed on May 10, 2002, now abandoned.

(60) Provisional application No. 60/290,237, filed on May 11, 2001.

(51) Int. Cl.
- *A01N 25/34* (2006.01)
- *A61K 8/02* (2006.01)
- *C11D 17/00* (2006.01)

(52) U.S. Cl. .................. 424/402; 424/401; 510/157; 510/151; 510/130

(58) Field of Classification Search .................. 424/402, 424/401; 510/157, 151, 130
See application file for complete search history.

(56) References Cited

U.S. PATENT DOCUMENTS

| | | | |
|---|---|---|---|
| 3,881,210 A | 5/1975 | Drach et al. |
| 4,112,167 A | 9/1978 | Dake et al. |
| 4,690,821 A | 9/1987 | Smith et al. |
| 4,904,524 A | 2/1990 | Yoh |
| 4,948,585 A | 8/1990 | Schlein |
| 5,055,216 A | 10/1991 | Johnson |
| 5,204,093 A | 4/1993 | Victor |
| 5,256,417 A | 10/1993 | Koltisko |
| 5,302,446 A | 4/1994 | Horn |
| 5,409,747 A | 4/1995 | Pearlstein et al. |
| 5,595,807 A | 1/1997 | Gooding, Jr. et al. |
| 5,629,081 A | 5/1997 | Richards et al. |
| 5,639,532 A | 6/1997 | Wells |
| 5,679,399 A | 10/1997 | Shlenker et al. |

(Continued)

FOREIGN PATENT DOCUMENTS

EP    1774980 A1  *  4/2007

(Continued)

OTHER PUBLICATIONS

Nakajima, Oct. 9, 1995, JP07-255630A, Raw machine translation.*

(Continued)

*Primary Examiner*—Gina C. Yu
(74) *Attorney, Agent, or Firm*—Kilpatrick Stockton LLP

(57) ABSTRACT

A wipe having at least two sides for applying a cleansing material and a drying material to a skin surface. The cleansing material may be applied to a first side of the wipe, and the drying material to a second side of the wipe. The first side of the wipe is used to clean a skin surface by rubbing the wipe across the skin surface. The first side of the wipe removes dirt, grease and other materials from the skin surface. The second side of the wipe removes any dirt, grease or other materials not removed by the first side of the wipe and the cleansing material. The second side of the wipe also leaves a substance having a powdery feel on the skin surface.

19 Claims, 3 Drawing Sheets

U.S. PATENT DOCUMENTS

| | | |
|---|---|---|
| 5,716,692 A | 2/1998 | Warner et al. |
| 5,817,379 A | 10/1998 | Rich et al. |
| 5,869,071 A | 2/1999 | Wieselman et al. |
| 5,945,090 A | 8/1999 | Randall et al. |
| 5,980,931 A | 11/1999 | Fowler et al. |
| 6,153,208 A | 11/2000 | McAtee et al. |
| 6,183,763 B1 | 2/2001 | Beerse et al. |
| 6,206,863 B1 | 3/2001 | Skewes et al. |
| 6,432,429 B1 * | 8/2002 | Maddern et al. ............ 424/402 |
| 6,440,437 B1 | 8/2002 | Krzysik et al. |
| 6,641,826 B2 | 11/2003 | Durden |

FOREIGN PATENT DOCUMENTS

JP 07-255630 * 10/1995

OTHER PUBLICATIONS

Poucher's Perfumes, Cosmetics and Soaps, 2000, Kluwer Academic Publishers, (10th ed by Hilda Butler), p. 170 and 482.*

Croda Brochure: Product Guide, 1998, Croda, Inc.

Picture of box and packaging of Shower to Shower®; Refreshing Body Cloths, distributed in the United States by Johnson & Johnson, Skillman, NJ.—admitted prior art.

* cited by examiner

TWO-SIDED WIPE FOR CLEANING AND DRYING A SKIN SURFACE

RELATED APPLICATIONS

This Application is a continuation of U.S. Non-provisional patent application Ser. No. 10/144,002 filed May 10, 2002, now abandoned which claims the benefit of U.S. Provisional Application No. 60/290,237, filed May 11, 2001, both of which are herein incorporated by this reference.

FIELD OF THE INVENTION

This invention relates to a consumer product for washing and drying a skin surface of a person, and more particularly to a wipe having two sides, one for cleaning a skin surface and the other side for drying the skin surface.

BACKGROUND OF THE INVENTION

Personal cleaning products have traditionally been marketed in a variety of forms such as bar soaps, creams, lotions, gels, body washes and wipes. Each of these products has achieved some degree of acceptance by most consumers. Wipes have been accepted by consumers as a medium for carrying and applying cleaning materials to a skin surface in situations where soaps and lotions are inconvenient to use. For example, wipes, commonly referred to as baby wipes, have been used by consumers for years as an aide in cleaning a babies while changing diapers or cleaning spills. Wipes have also been used in restaurants where meals, such as ribs, chickens and other foods, are eaten by hand. In yet another situation, wipes are used to clean elderly people who are bed ridden or otherwise unable to bathe often.

While wipes have been used in a variety of situations, the use of wipes is not favored by all consumers. Specifically, most wipes are used to clean a skin surface by rubbing the wipe on the skin surface. This action removes dirt, grease and other materials and applies a cleaning solution to the skin surface. Often, the skin surface is left with a wet feeling after application of the cleaning material that is uncomfortable to many consumers. Thus, many consumers are hesitant to use wipes after exercising and before redressing, such as after working out at a gym. While some cleaning solutions are alcohol based and thereby evaporate from the skin surface in a relatively short time after application, many consumers are not in favor the wet feeling that is left after use of a wipe.

Thus, a need exists for a single device which is disposable, inexpensive, transportable, and simple to use for cleaning a skin surface and leaving the surface with a more comfortable dry feeling.

SUMMARY OF THE INVENTION

This invention is directed to a device capable of applying a cleansing material and a drying material to a skin surface. In certain embodiments, the device is a wipe having a first side for applying the cleansing material and a second side for applying the drying material to a skin surface. The wipe may have a generally planar shape and be formed from any combination of materials. In one embodiment, the first and second sides of the wipe may be separated with an impermeable layer, which in certain embodiments may be a plastic film.

The wipe is used by first applying the cleansing material located on the first side of the wipe to a skin surface, such as a hand, arm, or other area. One method of applying the cleansing material is by rubbing the first side of the wipe on the skin surface. This action imparts the cleansing material on the skin surface and removes dirt, grease and other materials from the skin surface. The materials removed from the skin surface mix with the cleansing material on the wipe and, at times, adhere to the wipe itself.

The wipe is then configured so that the second side containing the drying material is exposed for application. This can be accomplished in numerous manners, and one method includes folding the wipe so that the first side is concealed and the second side is exposed. The drying material located on the second side of the wipe may then be applied to the wipe without threat that the cleansing material will be reapplied to the skin surface.

The drying material is applied to the skin surface from the second side of the wipe through numerous manners, one of which includes rubbing. The second side of the wipe removes dirt and other materials not removed by the first side of the wipe and removes the cleansing material. In certain embodiments, the second side of the wipe may also impart a substance having a powdery feel to the skin surface. This substance may give the skin surface the feeling of being clean and dry.

An advantage of this invention is that a wipe may be used to apply a cleansing material to a skin surface, remove the cleansing material from the skin surface, and dry the skin surface.

Another advantage of this invention is that a wipe may be used to apply a cleansing material to a skin surface, remove the cleansing material from the skin surface, and leave a powdery material on the skin surface.

Yet another advantage of this invention is that a single wipe may be used to disinfect a skin surface and to dry that same skin surface.

These and other features and advantages of the present invention will become apparent after review of the following drawings and detailed description of the disclosed embodiments.

DETAILED DESCRIPTION OF THE INVENTION

Figure 1:
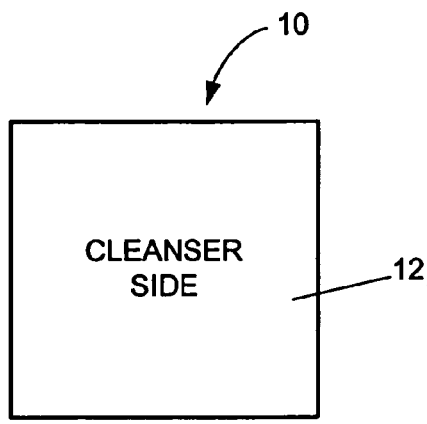
FIG. 1 is a top view of a first side, also referred to as a cleaner side, of a wipe of this invention.

This invention is a two-sided wipe 10, as shown in FIGS. 1-7, including a cleanser on one side and a drying and moisturizing agent on the other side. The wipe 10 may include, but is not limited to, a towelette, a tissue, or a wash cloth. Side I 12, also referred to as the cleaning side, of wipe 10 may include a cleanser for cleaning a skin surface. Preferably, Side I 12, the cleanser side, of wipe 10 includes a mild cleanser that is suitable for use in situations requiring frequent applications, including, but not limited to, geriatric use and hospital use.

A blend of surfactants provides the cleanser side 12 of wipe 10 with a moderately foaming cleanser having conditioning properties. Preferably, the cleanser includes, but is not limited to, approximately the following quantities of the following components:

| | |
|---|---|
| Disodium Oleth-3 Sulfosuccinate | 5.0 percent by weight; |
| Isostearamidopropyl Morpholine Lacate | 1.0 percent by weight; |
| Cocamidopropyl Betaine | 5.0 percent by weight; |
| Cocamide DEA Cocoyl Sarcosine | 2.0 percent by weight; |
| Lauramide DEA | 1.0 percent by weight; |
| Sucrose Coacoate | 2.5 percent by weight; |
| Germaben II | 0.3 percent by weight; |
| Water | 83.2 percent by weight; and |
| Fragrance | sufficient quantity. |

Further, the cleanser may include an antibacterial agent.

The cleanser set forth above may be produced by a thoroughly mixing the above disclosed materials. After thoroughly mixing the components, the mixture is heated to a temperature within the range from 50° Celsius to 60° Celsius. Once heated, the mixture is cooled by removing the heat source and further mixing the mixture. The pH of the mixture may be adjusted using citric acid. Once the mixture has adequately cooled, it may be applied to the first side 12 of wipe 10.

Alternatively, Side I 12 of wipe 10 may include a weaker cleanser than set forth above. Specifically, the alternative cleanser may be more mild than the cleanser set forth above and may be used safely with infants and other people susceptible to injury from strong cleansers. Further, the alternative cleanser does not produce a lather when applied to the skin. The alternative cleanser may include components such as, but not limited to, these materials in approximately the amounts shown:

| | |
|---|---|
| Propylene Glycol | 3.00 percent by weight; |
| Disodium Cocamphoiacete | 3.00 percent by weight; |
| Methylparaben | 0.15 percent by weight; |
| Fragrance | sufficient quantity; and |
| Water | sufficient quantity to 100.00 percent; |

The alternative cleanser may be produced by mixing all of the components listed above until the mixture is clear in appearance. Preferably, the pH may be adjusted to be within the range from 6.0 to 7.0 using citric acid. In yet another alternative formulation, alcohol may be removed from the mixture in order to provide a product which is relatively mild and capable of being applied on sensitive skin, such as on an infant's or elderly person's skin.

Side II 14, referred to as the finishing side of wipe 10, may include a drying agent to absorb the cleansing material applied from the Side I 12 of wipe 10. Preferably, Side II 14 includes a material having properties which dry and moisturize the skin surface and impart a pleasant powdery feeling to the skin. Side II 14 preferably is composed of materials including, but not limited to, materials in the following approximate proportions:

| | |
|---|---|
| Components Part A | |
| Cetearyl Alcohol | 2.00 percent by weight; |
| PRG-2 Myristyl Ether Propionate | 0.25 percent by weight; |
| Emulsifying Wax NF | 2.00 percent by weight; |
| Components Part B | |
| SDA 40 Alcohol | 75.50 percent by weight; |
| Polysorbate 80 (Crodalan AWS) | 0.25 percent by weight; |
| Benzophenone | 0.10 percent by weight; |
| Water | 11.50 percent by weight; |
| Components Part C | |
| PEG-15 Cocamine | 0.85 percent by weight; and |
| Components Part D | |
| Tapioca Flour | 8.00 percent by weight. |

This mixture is created by mixing the materials designated as Part A above and heating the materials to a temperature within the range from 60° Celsius to 65° Celsius. The materials designated as Part B above are mixed together and heated to a temperature within the range from 60° Celsius to 65° Celsius. The mixture formed by materials designated as Part A are mixed with the mixture composed of materials designated as Part B. The material labeled Part C above is then mixed with the mixture of Part A and Part B and cooled to a temperature of 60° Celsius. The material designated Part D above is then mixed with the mixture composed of Parts A, B, and C and cooled in order to apply the mixture to wipe 10.

The formula set forth above for the material to be applied to the finishing side 14 may be adjusted to increase or decrease the dryness of the material. Specifically, the amount of water and alcohol may be changed in order to produce a wetter or dryer finishing material. In another alternative embodiment, Part D of the finishing material may be composed of substances producing a powdery feel including, but not limited to, talc or corn starch rather than tapiocia flour. Additionally, the finishing material may include moisturizers and other materials providing beneficial effects to the skin which include, but are not limited to, vitamin E, emu oil, or aloe.

Figure 2:
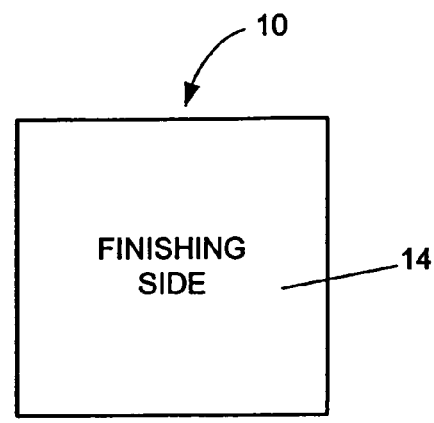
FIG. 2 is a bottom view of the wipe shown in FIG. 1 showing the finishing side of the wipe.
Figure 3:
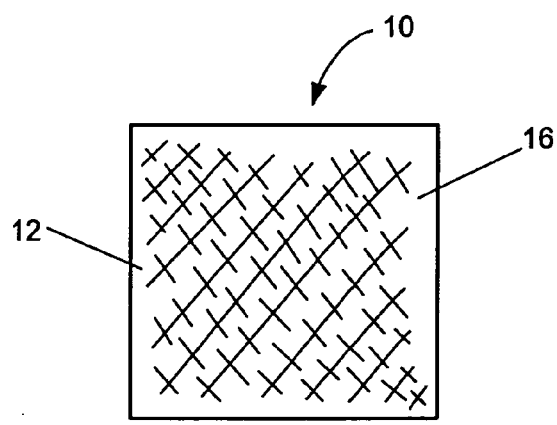
FIG. 3 is a top view of an embodiment of this invention including a textured surface.
Figure 4:
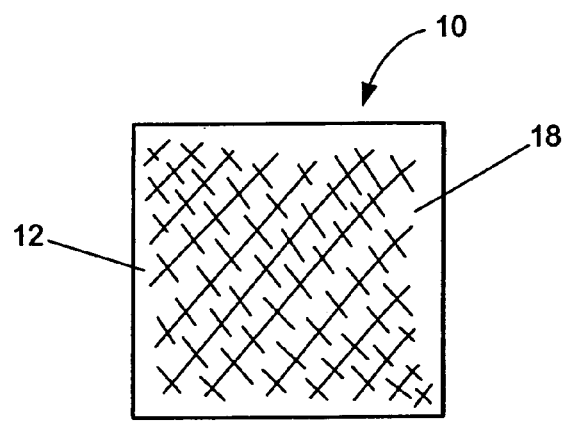
FIG. 4 is a bottom view of the wipe shown in FIG. 3 including a textured surface.
Figure 5:
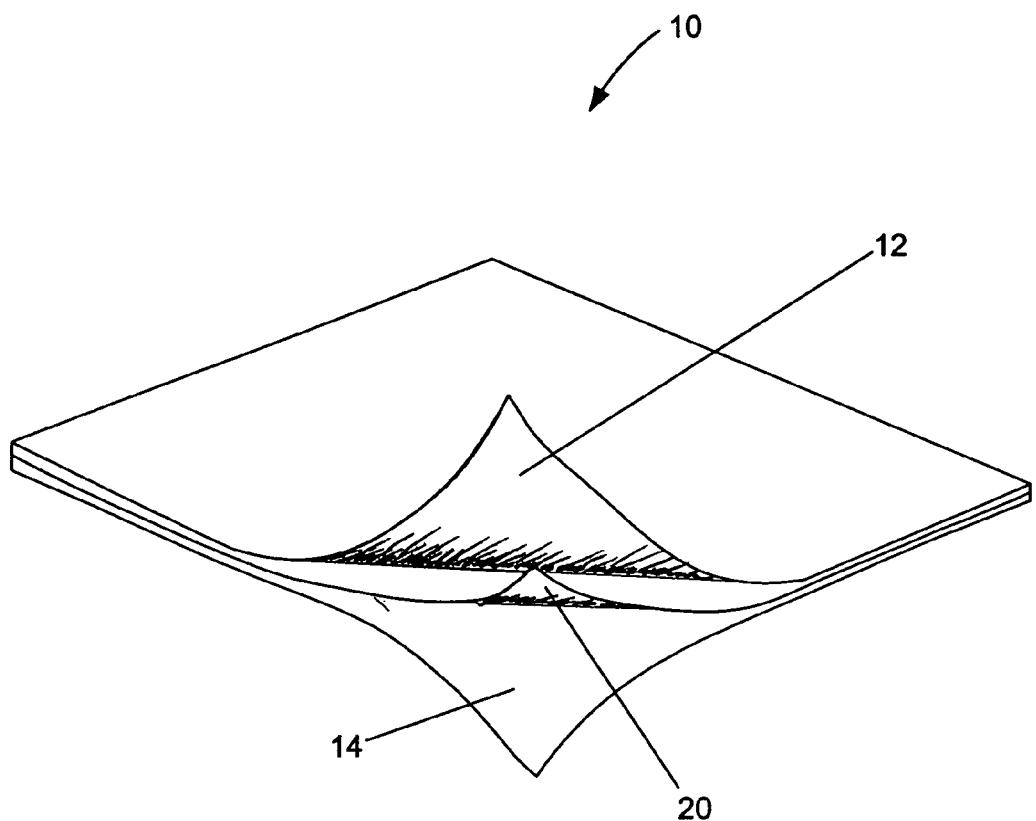
FIG. 5 is a perspective view of a wipe having a first side, an impermeable layer, and a second side, shown with the layers separated for easier viewing.

In one embodiment, the cleanser side 12 of wipe 10 may include a textured surface 16, as shown in FIG. 3, in order to enhance the wipe's ability to clean a skin surface. The textured surface 16 may have a well defined texture so that it is abrasive when applied to the skin surface of a user. Alternatively, the textured surface 16 of the fabric may not be abrasive. Instead, the fabric may be smooth. Likewise, the finishing side 14 may include a textured surface 18, as shown in FIG. 4, or a smooth surface, as shown in FIG. 2. However, it may be preferable, because of manufacturing efficiencies, to construct each side of the wipe out of the same material.

Wipe 10 may be composed of a thin planar material composed of a cleanser side 12, designated as Side I, a finishing side 14, designated as Side II, and an impermeable layer 20 positioned between Sides I and II. In one embodiment, impermeable layer 20 is a plastic film. Impermeable layer 20 prevents the cleanser material located on Side I 12 from interacting and mixing with the finishing material located on Side II 14. Further, impermeable layer 20 prohibits dirt and bacteria from traveling from the cleanser side 12 to the finishing side 14. Preferably, wipe 10 is about 16 inches square and 1/32 inch thick. However, wipe 10 may be any size or thickness enabling the performance of this invention in accord with the objectives set forth herein. Alternatively, wipe 10 may be composed of a single piece of material, having first and second sides, wherein the material is impervious, or nearly impervious, to the cleanser and the finishing material in order to prevent mixing of the materials and contamination of either side of wipe 10.

Figure 6:
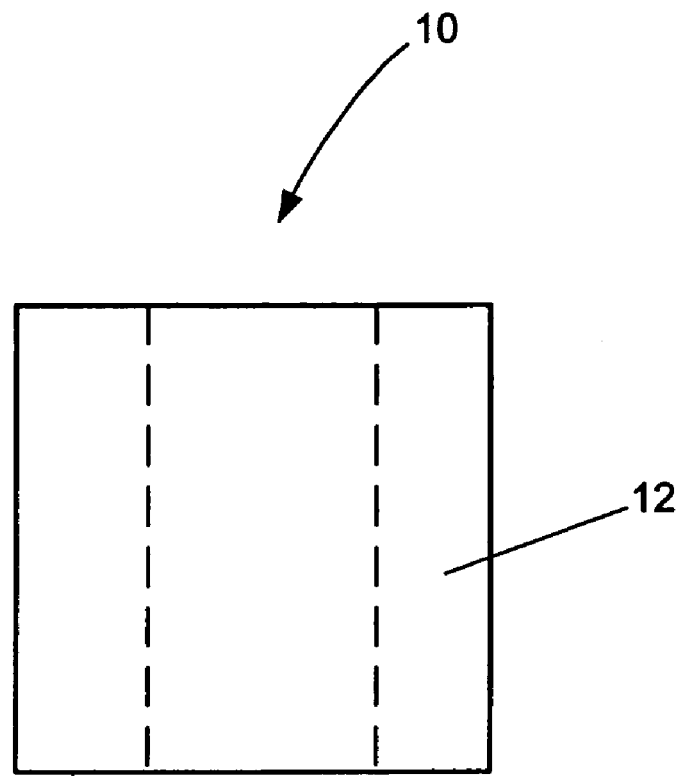
FIG. 6 is a top view of a wipe having score marks for folding the wipe.
Figure 7:
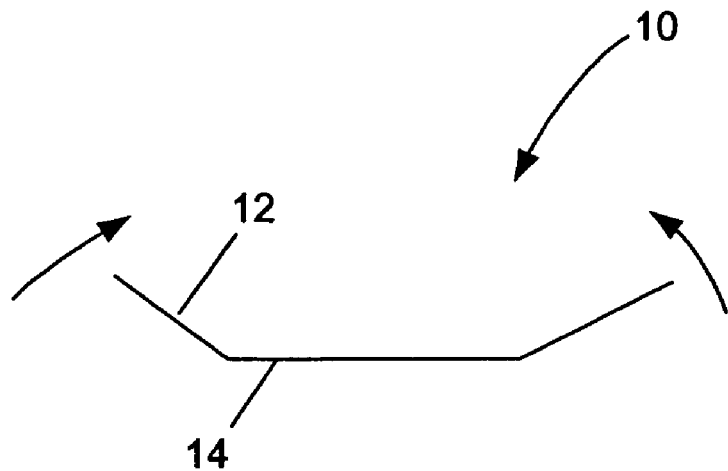
FIG. 7 is a front view of a wipe showing portions of the wipe being folded into position for applying a second material located on the second side of the wipe to a skin surface.

Preferably, wipe 10 is packaged and marketed so that the cleanser side 12 of wipe 10 does not contact the finishing side 14. This may be accomplished by folding the outside quarter of two opposing sides of wipe 10 and folding each quarter toward the center of wipe 10, thereby covering the inner one half of wipe 10, as shown in FIGS. 6 and 7. Alternatively, wipe 10 could be folded along its centerline. In the alternative embodiment, one half of wipe 10 is folded onto the other side of wipe 10 thereby fully enclosing and protecting one side of wipe 10 while exposing the other side. Other methods of folding wipe 10 may be used in order to prevent mixing of the cleanser with the finishing material.

Wipe 10 is used to first clean a surface of the body with the cleanser side 12 of wipe 10. Preferably, each side of wipe 10 is labeled either "cleanser side" or "finishing side," as shown in FIGS. 1 and 2, or some other appropriate designation, in order to quickly alert the user to the purpose of each side of wipe 10. First, the user must fold wipe 10, if it is not already folded, such as in the center of wipe 10, so that only the cleanser side 12 of wipe 10 is exposed. The user then is able to apply the cleanser material to the desired skin surface in order to clean the surface.

Once the user has thoroughly cleaned the desired skin surface, the user then refolds wipe 10 so that the only the finishing side 14 is exposed. Preferably, the user accomplishes this by folding wipe 10 down the center line. The user than removes the cleanser material and lather from the skin surface by rubbing wipe 10 across the skin surface containing the cleanser material. The finishing side 14 of wipe 10 removes excess dirt not absorbed or retained by the cleanser side 12 of wipe 10 at least partially by absorbing the cleanser material and lather and at least partially by retaining the later and cleanser on the surface of the finishing side 14 of wipe 10. Further, the lather remaining on the skin surface from application of the cleanser located on the first side 12 of wipe 10 is absorbed by the cloth material on the finishing side 14 and is mixed with the finishing material remaining on wipe 10. The cleanser may also be removed from the skin surface through evaporation. Once the user has finished using wipe 10, it is preferable that the user dispose wipe 10 in a trash receptacle.

While various embodiments of this invention have been described above, these descriptions are given for purposes of illustration and explanation. Variations, changes, modifications and departures from the systems and methods disclosed above may be adopted without departure from the spirit and scope of this invention.

We claim:

1. A wipe for cleaning and drying a skin surface, comprising:
    a planar sheet comprising a first side and a second side;
    wherein the first side comprises a first material comprising a cleanser; and
    wherein the second side comprises a second material different from the first material, comprising a drying agent and a powdery substance.

2. The wipe of claim 1, further comprising an impervious layer positioned between the first and second side of the planar sheet.

3. The wipe of claim 2, wherein the impervious layer is a plastic film.

4. The wipe of claim 1, wherein the first side comprises a textured surface.

5. The wipe of claim 1, wherein the second side comprises a textured surface.

6. The wipe of claim 1, wherein the first side comprises a mixture of cocamidopropyl betaine, cocamide DEA cocoyl sarcosine, lauramide DEA, water and fragrance.

7. The wipe of claim 6, wherein the first side comprises a mixture of about 5 percent disodium oleth-3 sulfosucinate by weight, about 5 percent cocamidopropyl betaine by weight, about 2 percent cocamide DEA cocoyl sarcosine by weight, about 1 percent lauramide DEA by weight, about 2.5 percent sucrose coacoate by weight, about 83.2 percent water by weight and fragrance.

8. The wipe of claim 1, wherein the first side comprises a mixture of propylene glycol, methylparaben, fragrance, and water.

9. The wipe of claim 8, wherein the first side comprises a mixture of about 3 percent propylene glycol by weight, about 3 percent disodium cocamphoiacete by weight, about 0.15 percent methylparaben by weight, fragrance, and water.

10. The wipe of claim 1, wherein the second side comprises a mixture of cetearyl alcohol, PRG-2 myristyl ether propionate, emulsifying wax NF, SDA 40 alcohol, polysorbate 80, benzophenone, water, PEG-15 cocamine, and tapioca flour.

11. The wipe of claim 10, wherein the second side comprises a mixture of about 2 percent cetearyl alcohol by weight, about 2 percent emulsifying wax NF by weight, about 75.5 percent SDA 40 alcohol by weight, about 0.25 percent polysorbate 80 by weight, about 0.10 benzophenone by weight, about 11.5 percent water by weight, about 0.85 percent PEG-15 cocamine by weight, and about 8 percent tapioca flour by weight.

12. The wipe of claim 1, further comprising at least one score mark for folding the wipe so that the first side does not contact the second side.

13. A method for cleaning and drying a skin surface, comprising:
    (a) applying a cleanser to a skin surface with a first side of a wipe, the wipe comprising, a planar sheet comprising the first side and a second side; wherein the first side comprises a first material comprising the cleanser; and wherein the second side comprises a second material different from the first material, comprising a drying agent and a powdery substance; and
    (b) applying the drying agent and powdery substance to the skin surface with the second side of the wipe.

14. The method of cleaning and drying a skin surface of claim 13, wherein applying the cleanser to the skin surface with the first side of the wipe comprises applying the cleanser to the skin surface with a textured surface of the first side of the wipe.

15. The method of cleaning and drying a skin surface of claim 13, wherein applying the drying agent and powdery substance to the skin surface with the second side of the wipe comprises applying the drying agent and powdery substance to the skin surface with a textured surface of the second side of the wipe.

16. The method of cleaning and drying a skin surface of claim 13, wherein applying the cleanser to the skin surface comprises applying a mixture comprising cocamidopropyl betaine, cocamide DEA cocoyl sarcosine, lauramide DEA, water and fragrance to the skin surface.

17. The method of cleaning and drying a skin surface of claim 16, wherein applying the mixture comprising cocamidopropyl betaine, cocamide DEA cocoyl sarcosine, lauramide DEA, water and fragrance to the skin surface comprises applying a mixture comprising about 5 percent disodium oleth-3 sulfosucinate by weight, about 5 percent cocamidopropyl betaine by weight, about 2 percent cocamide DEA cocoyl sarcosine by weight, about 1 percent lauramide DEA by weight, about 2.5 percent sucrose coacoate by weight, about 83.2 percent water by weight and fragrance to the skin surface.

18. The method of cleaning and drying a skin surface of claim 13, wherein applying the drying agent and powdery substance to the skin surface comprises applying a mixture comprising cetearyl alcohol, PRG-2 myristyl ether propionate, emulsifying wax NF, SDA 40 alcohol, polysorbate 80, benzophenone, water, PEG-15 cocamine, and tapioca flour to the skin surface.

19. The method of cleaning and drying a skin surface of claim 18, wherein applying the mixture comprising cetearyl alcohol, PRG-2 myristyl ether propionate, emulsifying wax NF, SDA 40 alcohol, polysorbate 80, benzophenone, water, PEG-15 cocamine, and tapioca flour to the skin surface comprises applying a mixture comprising about 2 percent cetearyl alcohol by weight, about 2 percent emulsifying wax NF by weight, about 75.5 percent SDA 40 alcohol by weight, about 0.25 percent polysorbate 80 by weight, about 0.10 benzophenone by weight, about 11.5 percent water by weight, about 0.85 percent PEG-15 cocamine by weight, and about 8 percent tapioca flour by weight to the skin surface.

\* \* \* \* \*